(12) United States Patent
Geng et al.

(10) Patent No.: US 11,013,397 B2
(45) Date of Patent: May 25, 2021

(54) ENDOSCOPE APPARATUS AND CONTROLLING METHOD THEREOF

(71) Applicant: BOE Technology Group Co., Ltd., Beijing (CN)

(72) Inventors: Lihua Geng, Beijing (CN); Xiao Zhang, Beijing (CN); Zhiguo Zhang, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 362 days.

(21) Appl. No.: 16/005,293

(22) Filed: Jun. 11, 2018

(65) Prior Publication Data
US 2019/0200849 A1 Jul. 4, 2019

(30) Foreign Application Priority Data
Jan. 2, 2018 (CN) .......................... 201810002481.8

(51) Int. Cl.
A61B 1/045 (2006.01)
A61B 1/00 (2006.01)
(Continued)

(52) U.S. Cl.
CPC .......... *A61B 1/045* (2013.01); *A61B 1/00006* (2013.01); *A61B 1/0019* (2013.01); *A61B 1/00096* (2013.01); *A61B 1/00009* (2013.01); *A61B 1/00039* (2013.01); *A61B 1/00045* (2013.01); *A61B 1/00055* (2013.01); *A61B 1/05* (2013.01); *G06T 2207/10068* (2013.01); *H04N 2005/2255* (2013.01)

(58) Field of Classification Search
CPC combination set(s) only.
See application file for complete search history.

(56) References Cited

U.S. PATENT DOCUMENTS

| 5,098,426 A * | 3/1992 | Sklar | A61F 9/008 606/5 |
| 7,853,050 B2 * | 12/2010 | Wang | G06F 3/012 382/118 |

(Continued)

FOREIGN PATENT DOCUMENTS

| CN | 1694045 A | 11/2005 |
| CN | 104055478 A | 9/2014 |

(Continued)

OTHER PUBLICATIONS

Office Action issued in corresponding Chinese Patent Application No. 201810002481.8, dated Apr. 28, 2019.
(Continued)

Primary Examiner — John P Leubecker
Assistant Examiner — Shankar Raj Ghimire
(74) Attorney, Agent, or Firm — McDermott Will & Emery LLP

(57) ABSTRACT

Embodiments of the present disclosure provide an endoscope apparatus and a method for controlling the endoscope apparatus. The endoscope apparatus may comprise an image collector, configured to collect an image for an eyeball of a user; a controller, configured to calculate a parameter for adjusting an endoscope lens of an endoscope based on the collected image; and the endoscope, configured to adjust the endoscope lens according to the parameter.

4 Claims, 5 Drawing Sheets

(51) Int. Cl.
*A61B 1/05* (2006.01)
*H04N 5/225* (2006.01)

(56) References Cited

U.S. PATENT DOCUMENTS

| | | | | |
|---|---|---|---|---|
| 10,278,782 | B2* | 5/2019 | Jarc | G02B 27/0093 |
| 10,583,068 | B2* | 3/2020 | Du | A61H 5/00 |
| 2002/0013573 | A1* | 1/2002 | Telfair | A61B 3/113 |
| | | | | 606/5 |
| 2012/0147328 | A1* | 6/2012 | Yahav | H04N 13/383 |
| | | | | 351/210 |
| 2015/0099926 | A1* | 4/2015 | Davidson | A61B 34/20 |
| | | | | 600/103 |
| 2017/0172675 | A1* | 6/2017 | Jarc | A61B 90/37 |
| 2018/0092706 | A1* | 4/2018 | Anderson | A61B 34/30 |
| 2018/0120932 | A1* | 5/2018 | Sengelaub | G06K 9/0061 |
| 2019/0200998 | A1* | 7/2019 | Shelton, IV | A61B 1/0661 |
| 2020/0166742 | A1* | 5/2020 | Peyman | G02C 7/085 |
| 2020/0214559 | A1* | 7/2020 | Krueger | A42B 3/046 |

FOREIGN PATENT DOCUMENTS

| | | |
|---|---|---|
| CN | 204215097 U | 3/2015 |
| CN | 205359411 U | 7/2016 |
| CN | 106456148 A | 2/2017 |
| CN | 102727309 A | 8/2017 |
| CN | 107049210 A | 8/2017 |
| EP | 3119286 A4 | 4/2018 |
| WO | 2015/143067 A1 | 9/2015 |

OTHER PUBLICATIONS

Office Action issued in corresponding Chinese Patent Application No. 201810002481.8, dated Jan. 15, 2020.

* cited by examiner

ENDOSCOPE APPARATUS AND CONTROLLING METHOD THEREOF

CROSS-REFERENCE TO RELATED APPLICATION

This application claims the priority of Chinese Patent Application No. 201810002481.8 filed on Jan. 2, 2018, the disclosure of which is incorporated herein by reference in its entirety as part of this application.

TECHNICAL FIELD

Embodiments of the present disclosure relate to the field of data processing technology, and in particular, to an endoscope apparatus and a controlling method thereof.

BACKGROUND

With a development of modern medical science and technology, the application of endoscopic technology has important significance.

SUMMARY

According to an aspect of embodiments of the present disclosure, there is provided an endoscope apparatus, comprising: an image collector, configured to collect an image for an eyeball of a user; a controller, configured to calculate a parameter for adjusting an endoscope lens of an endoscope based on the collected image; and the endoscope, configured to adjust the endoscope lens according to the parameter.

For example, the controller is further configured to: calculate a current position of the eyeball based on the collected image; compare the current position with an initial position of the eyeball, and determine whether there is a change in the position of the eyeball according to a comparison result; and calculate the parameter for adjusting the endoscope lens based on the current position and the initial position, in response to determining that there is a change in the position of the eyeball.

For another example, the image collector is further configured to collect the image for the eyeball of the user who is staring at a preset positioning point; and the controller is further configured to calculate an initial position of the eyeball according to a position information of the preset positioning point and the collected image.

For another example, the endoscope comprises: an rod for operating an endoscope lens, comprising a body, an adjustable sub-rod, a first motor and a second motor, wherein a first end of the adjustable sub-rod is fixed to the body rotatably and retractably, and the first motor is configured to drive the adjustable sub-rod to stretch or retract in an axial direction, and the second motor is configured to drive the adjustable sub-rod to rotate about the first end; the endoscope lens, disposed on the adjustable sub-rod and configured to collect an endoscopic image; and a controlling device, configured to control at least one of the first motor and the second motor according to the parameter for adjusting the endoscope lens.

For another example, the endoscope further comprises a pressure sensor and an alarm device; wherein the pressure sensor is disposed at a second end of the adjustable sub-rod and configured to detect an external pressure applied on the second end of the adjustable sub-rod and to convert the detected external pressure into an electrical signal; the controlling device is configured to calculate a pressure data according to the electrical signal, and to send an alarm prompting information to the alarm device in response to the pressure data exceeding a preset pressure threshold; and the alarm device is configured to send an alarm in response to receiving the alarm prompting information.

For another example, the controlling device is further configured to: receive the endoscopic image collected by the endoscopic lens; and send the endoscopic image to the controller.

For another example, the endoscope apparatus may further comprise: a display, coupled to the controller, and configured to display the endoscopic image.

According to another aspect of the present disclosure, there is provided a method for controlling an endoscope, comprising: collecting an image for an eyeball of a user; calculating a parameter for adjusting an endoscope lens of the endoscope based on the collected image; and adjusting the endoscope lens according to the parameter.

For example, calculating the parameter for adjusting the endoscope lens of the endoscope based on the collected image comprises: calculating a current position of the eyeball based on the collected image; comparing the current position with an initial position of the eyeball, and determining whether there is a change in the position of the eyeball according to a comparison result; and calculating the parameter for adjusting the endoscope lens based on the current position and the initial position, in response to determining that there is a change in the position of the eyeball.

For another example, the method may further comprise: collecting the image for the eyeball of the user who is staring at a preset positioning point; and calculating an initial position of the eyeball according to a position information of the preset positioning point and the collected image.

It is understood that other embodiments and configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The above and other features and advantages of the present disclosure will become more apparent and a more comprehensive understanding of the present disclosure can be obtained, by describing in detail exemplary embodiments thereof with reference to the accompanying drawings, in which.

DETAILED DESCRIPTION

In order to understand the above objects, features and advantages of the present invention clearly, embodiments of the present invention will be further described in detail below with reference to the accompanying drawings.

It should be noted that the terms of "first", "second" and the like used in the embodiments of the present disclosure do not indicate any order, quantity, or importance, but are only used to distinguish one component from another.

Figure 1:
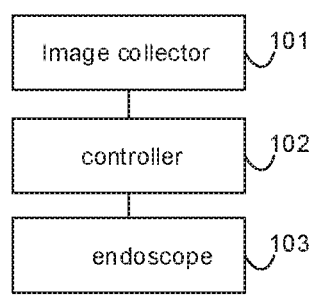
FIG. 1 shows a schematic structural view of an endoscope apparatus according to an embodiment of the present disclosure.

An aspect of an embodiment of the present disclosure provides an endoscope apparatus that enables an automatic, real-time adjustment of an endoscopic lens in the endoscope apparatus during an endoscopic surgery. FIG. 1 shows a schematic structural view of an endoscope apparatus according to an embodiment of the present disclosure. As shown in FIG. 1, the endoscope apparatus 10 according to the embodiment of the present disclosure may comprise an image collector 101 configured to collect an image for an eyeball of a user.

For example, the user herein may be the chief surgeon of the endoscopic surgery, or a dedicated operator for the endoscope apparatus, or may be another participant in the endoscopic surgery, which is not limited herein. When the user is the chief surgeon of the endoscopic surgery, the adjustment of the endoscope lens can be made to coincide with changes in the image for the eyeball of the surgeon, making the operation more efficient.

For example, the image collector 101 may comprise an image collecting device such as a camera for collecting the image of the eyeball. Of course, in addition to the camera, other devices that can collect images can also be employed, which are not limited here. In addition, for example, the position for disposing the image collector 101 may be arbitrary, as long as the image for the eyeball of the user can be accurately collected and the position is stable, so that the change of the eyeball's position can be accurately calculated when the position for the pupil in the eyeball image changes.

The endoscope apparatus 10 may also include a controller 102. The controller 102 may be connected to the image collector 101 wirelessly or wiredly, and configured to calculate a parameter for adjusting an endoscope lens of an endoscope based on the collected image. For example, the parameter may be calculated based on changes in the eyeball images.

The endoscope apparatus 10 may also include an endoscope 103. The endoscope 103 has an endoscope lens and can be wirelessly or wiredly connected to the controller 102. The endoscope 103 is configured to adjust the endoscope lens according to the parameter. For example, the parameter may include a position parameter that the endoscope lens needs to adjust. According to the position parameter, the endoscope lens can be controlled to change its position.

According to the endoscope apparatus of the embodiment of the present disclosure, the user's eyeball image is tracked to identify the change of the operation part to be focused. Thus, an automatic and real time adjustment for the operation part via the user is enabled by adjusting a shooting direction and an angle of the endoscope lens automatically, which improves the operation efficiency.

Figure 2:
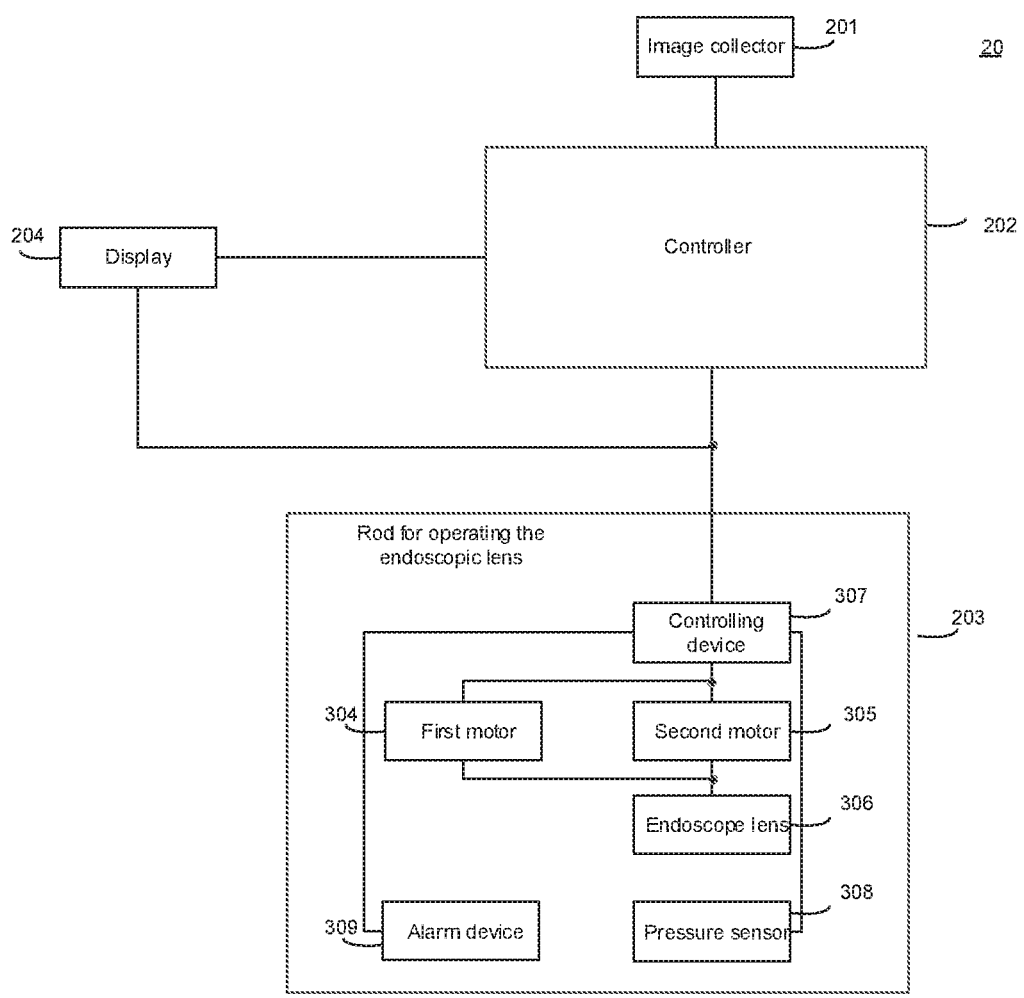
FIG. 2 shows a schematic structural view of an endoscope apparatus according to another embodiment of the present disclosure.

FIG. 2 shows a schematic structural view of an endoscope apparatus according to another embodiment of the present disclosure. As shown in FIG. 2, the endoscope apparatus 20 according to another embodiment of the present disclosure may include an image collector 201, configured to collect an image for an eyeball of a user; and a controller 202, coupled with the image collector 201 wirelessly or wiredly, and configured to calculate a parameter for adjusting an endoscope lens of an endoscope based on the collected image. For example, the controller 202 may be collect a position information for the eyeball of the user, and identify or determine the user's intention for the targeted observation area.

For example, the eyeball of the user can be initially positioned. Since different users and different distances may have different results on determining the eyeball position, in order to improve the accuracy for determining the eyeball position, the initial positioning is required. Thus, the image collector 201 is also configured to collect the image for the eyeball of the user who is staring at a preset positioning point. The controller 201 is further configured to calculate an initial position of the eyeball according to a position information of the preset positioning point and the collected image, so as to complete the initial positioning of the eyeball. This will facilitate in the subsequent processes for comparing the eyeball images and processing data.

Figure 3:
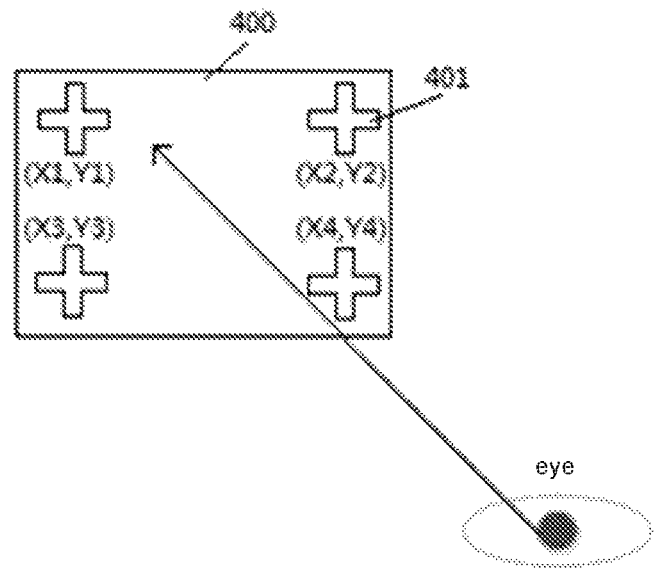
FIG. 3 shows an example schematic diagram of determining an initial position according to an embodiment of the present disclosure.

FIG. 3 shows an example schematic diagram of determining an initial position according to an embodiment of the present disclosure. As shown in FIG. 2, the endoscope apparatus may further comprise a display 204 coupled with the controller 202 wirelessly or wiredly. Initially, the controller 202 can control the display 204 to display a prompting image at the preset positioning point (such as, at a curse icon 401 shown in FIG. 3). In this embodiment, for example, there are four preset positioning points, which are respectively located at the upper left corner, the lower left corner, the upper right corner, and the lower right corner of the display 204. Starting from the upper left corner, the prompting image is displayed in clockwise order and continues for a first preset time, for example, 5s. In the process of displaying the prompting image, the user needs to stare at the prompting image. When the user is staring at each of the four positioning points, the controller 202 records the position information of the eyeball, and controls the image collector 201 to collect the eyeball image at this time. The controller 202 associates the eyeball images with coordinates (X1, Y1), (X2, Y2), (X3, Y3) and (X4, Y4) of the corresponding preset positioning points, to obtain an association relationship between the eyeball images and respective positioning points, wherein X is the abscissa and Y is the ordinate. For example, the association relationship may be a relationship between the position of each preset positioning point and the pupil position in the eyeball image which is collected when the user stares at corresponding preset positioning point. By using the association relationship, the pupil position in the eyeball image which is collected when the user stares at a center point of the display 204 can be calculated, thereby being used as the initial position of the eyeball. Of course, this is only an example of an embodiment, and those skilled in the art can know that there may be other positioning methods besides the initial positioning method of the eyeball. For example, the prompting image may be displayed at the center of the display 204 at the beginning, and the eyeball image when the user looks at the prompting image displayed at the center of the display 204 is directly collected as a criterion for calculating the initial position. Of course, in dealing with the eyeball image, the pupil can be used as a marker for positioning. Persons skilled in the art can understand that other markers can be applied to the present disclosure as long as positioning functions can be implemented, and details are not described herein again.

For example, the controller 202 may be configured to calculate the current position of the eyeball based on the collected image. For example, after the initial positioning of the eyeball is completed, the controller 202 tracks the change in the position of the eyeball in real time and calculates the current position of the eyeball. For example, the calculation of the current position may include converting the pupil position in the image to coordinate information of a position when the user stares at the corresponding position of the display 204, which is expressed as (Xt, Yt).

Figure 4:
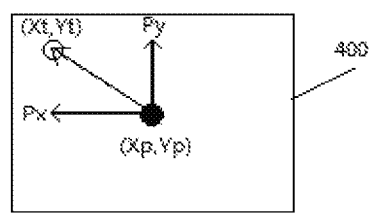
FIG. 4 shows an exemplary schematic diagram of calculating a parameter for adjusting an endoscope lens of the endoscope according to an embodiment of the present disclosure.

The controller 202 may also compare the current position with an initial position of the eyeball, and determine whether there is a change in the position of the eyeball according to a comparison result. For example, the controller 202 compares the difference between the current position and the initial position in real-time (which can be expressed by the coordinates (Xp, Yp)). When there is a change in the position of the eyeball and the change continues for a second preset time (for example, 3s, in order to exclude unconscious movements of the eyeball), the parameter for adjusting the lens can be calculated based on the current position and the initial position. For example, the difference between the current position and the initial position is calculated, for example, (Xt,Yt)-(Xp,Yp). Then, the numbers of pixels by which the endoscope lens should be horizontally and vertically adjusted are calculated according to the difference, such as (Px, Py), as shown in FIG. 4.

For example, the controller 202 may also be connected to the image collector 201 via a connection interface to receive the collected image. For example, the connection interface may be an interface such as an HDMI (High Definition Multimedia Interface), an LVDS (Low-Voltage Differential Signaling) interface, or a DP (Display Port) interface.

The controller 202 may also be connected to the endoscope 203 wirelessly or wiredly, so as to send the parameters for adjusting the endoscopic lens to the endoscope 203. For example, the numbers of pixels (Px, Py) by which the endoscope lens should be horizontally and vertically adjusted is transmitted to the endoscope 203.

The endoscope 203 can adjust the endoscope lens 306 according to the parameters.

Figure 5:
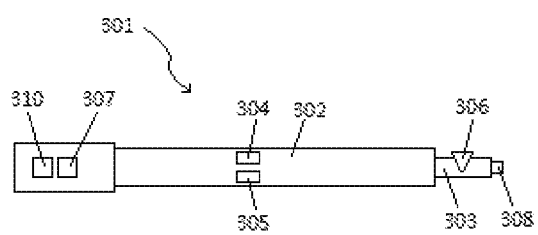
FIG. 5 shows a schematic structural view of a rod for operating the endoscope lens in the endoscope apparatus according to an embodiment of the present disclosure.

For another example, the endoscope 203 comprises: an rod for operating an endoscope lens 301, comprising a body 302, an adjustable sub-rod 303, a first motor 304 and a second motor 305. A first end of the adjustable sub-rod 303 is fixed to the body 302 rotatably and retractably, and the first motor 304 is configured to drive the adjustable sub-rod 303 to stretch or retract in an axial direction, and the second motor 305 is configured to drive the adjustable sub-rod 303 to rotate about the first end. The rod 301 can control the adjustment of the endoscope lens 306 according to the result of the eyeball tracking via the controller 200, so as to achieve the display of the operation part expected by the user, as shown in FIG. 5. The retractable displacement of the endoscope lens 306 is controlled by the first motor 304, and the rotational displacement of the endoscope lens 306 is controlled by the second motor 305. The first motor 304 and the second motor 305 are controlled by the controlling device 307.

The endoscope lens 306 may be disposed on the adjustable sub-rod 303 for collecting an endoscopic image, such as a tissue image inside the human body. For example, as shown in FIG. 5, an endoscope lens 306 may be mounted on a second end of the adjustable sub-rod 303. The adjustable sub-rod 303 may adjust the shooting direction of the endoscope lens 306 by a rotating and stretching or retracting movement. The collected endoscopic image can be displayed on the display 204. The shooting direction will be moved transversely if the adjustable sub-rod 303 stretches or retracts. In particular, when the adjustable sub-rod 303 stretches, the shooting direction moves to the right, and when the adjustable sub-rod 303 retracts, the shooting direction moves to the left. Similarly, the shooting direction 303 will be moved vertically if the adjustable sub-rod 303 rotates, and the collected image will be displayed on the display 204. In particular, when the adjustable sub-rod 303 rotates in a clockwise direction, the shooting direction moves downwardly, and when the adjustable sub-rod 303 rotates in a counterclockwise direction, the shooting direction moves upwardly.

The endoscope 203 may further comprise a controlling device 307, configured to control at least one of the first motor 304 and the second motor 305 according to the parameter for adjusting the endoscope lens, so as to enable the endoscopic lens 306 pointing at a position expected by the user. Thus, the moving direction and amplitude of the collected endoscopic image can be determined by the moving direction and amplitude of the rotation and stretching or retracting of the adjustable sub-rod 303. The movement of the adjustable sub-rod 303 is controlled by the first motor 304 and the second motor 305, and the first motor 304 and the second motor 305 are controlled by the controlling device 307. For example, depending on the numbers of pixels (Px, Py) by which the image collected via the endoscopic lens should be adjusted transversely and vertically, the amplitude for adjusting the endoscope lens 306 transversely and vertically can be calculated. Then, the first motor 304 and/or the second motor 305 can be controlled to rotate. For example, when Px is a positive value, the adjustable sub-rod 303 is controlled to retract, and when Px is a negative value, the adjustable sub-rod 303 is controlled to stretch. When Py is a positive value, the adjustable sub-rod 303 is controlled to rotate counterclockwise (referring to FIG. 5 as a reference), and when Py is a negative value, the adjustable sub-rod 303 is controlled to rotate clockwise (referring to FIG. 5 as a reference). Certainly, such controlling method is merely an example. The controlling of the adjustable sub-rod 303 can be adjusted if necessary, and the details are not described herein.

For another example, the endoscope 203 may further comprise a pressure sensor 308 and an alarm device 309. The pressure sensor 308 is disposed at the second end of the adjustable sub-rod 303 and configured to detect an external pressure applied on the second end of the adjustable sub-rod 303 and to convert the detected external pressure into an electrical signal. The controlling device 307 is configured to calculate a pressure data according to the electrical signal, and to send an alarm prompting information to the alarm device in response to the pressure data exceeding a preset pressure threshold. It should be noted that the preset pressure threshold can be set as needed, and are not limited herein.

The alarm device 309 is configured to send an alarm in response to receiving the alarm prompting information.

Therefore, the alarm device 303 is used to prevent the influence of the movement of the adjustable sub-rod 303 on human tissues. Since the pressure sensor 308 is installed at the top of the adjustable sub-rod 303, when the adjustable sub-rod 303 is in conflict with human tissues during its movement, the pressure at the top of the adjustable sub-rod 303 increases. When the pressure increases to the preset pressure threshold, the controlling device 307 notifies the alarm device 309 to send an alarm to prevent damage to human tissues.

For example, the controlling device 307 may also be configured to be wirelessly or wiredly coupled to the controller 202, so as to receive the parameters for adjusting the endoscopic lens, such as (Px, Py). The controlling device 307 can also be wirelessly or wiredly coupled to the endoscope lens 306, so as to receive the endoscopic image collected by the endoscope lens. The controlling device 307 can also receive the endoscopic image and send the endoscopic image to the controller 202.

For example, the display 204 may be wirelessly or wiredly coupled to the controlling device 307 to display the endoscopic image. Under a normal operation, the endoscope lens 306 collects the endoscopic image of the interested region and outputs it to the controlling device 307. The controlling device 307 processes the endoscopic image and transmits it to the display 204 for displaying.

Figure 6:
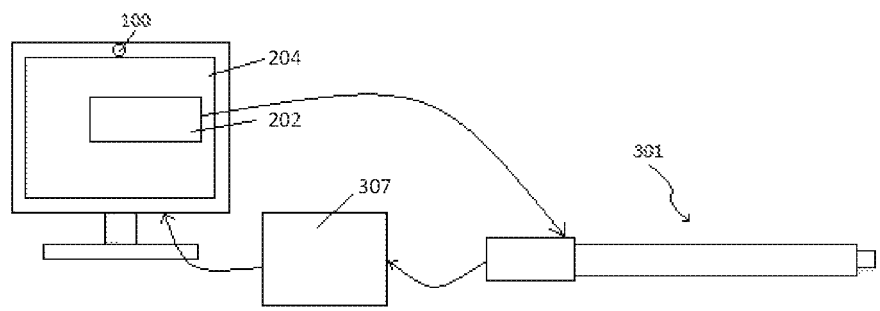
FIG. 6 shows a schematic diagram illustrating a structural relationship among an image collector, a display, a controller, and an endoscope in the endoscope apparatus according to an embodiment of the present disclosure.

For example, as shown in FIG. 6, the image collector 100 may be installed at a center position on the upper portion of the display 204. For example, the controller 202 may also be installed inside the display 204 so as to form an integrated machine having a controlling function. In addition, the rod for operating the endoscopic lens 301 may be equipped with an endoscope lens 306 and a corresponding adjustment mechanism.

It can be seen from the above description that the endoscope apparatus and the controlling method thereof provided by the embodiments of the present disclosure identify the change of the interested operation part by tracking the image for the eyeball of the user, and enable an automatic and real-time adjustment for the operation part via the user by adjusting the shooting direction and angle of the endoscopic lens automatically. This ensures that the operation expected by the user can always stays in the center of the display, which improves the operation efficiency.

Figure 7:
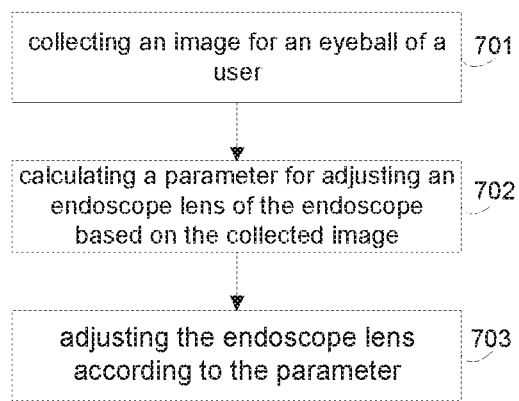
FIG. 7 shows a flowchart illustrating a method for controlling an endoscope according to an embodiment of the present disclosure.

Another aspect of an embodiment of the present disclosure, there is provide a method for controlling an endoscope. FIG. 7 shows a flowchart illustrating a method for controlling an endoscope according to an embodiment of the present disclosure. As shown in FIG. 7, a controlling method according to an embodiment of the present disclosure may include the following steps.

In step 701, an image for an eyeball of a user is collected.

In step 702, a parameter for adjusting an endoscope lens of the endoscope is calculated based on the collected image.

In step 703, the endoscope lens is adjusted according to the parameter.

According to the method for controlling the endoscope of an embodiment of the present disclosure, the change of the interested operation part may be identified by tracking the image for the eyeball of the user, and an automatic and real-time adjustment for the operation part via the user may be enabled by adjusting the shooting direction and angle of the endoscopic lens automatically, which improves the operation efficiency.

Figure 8:
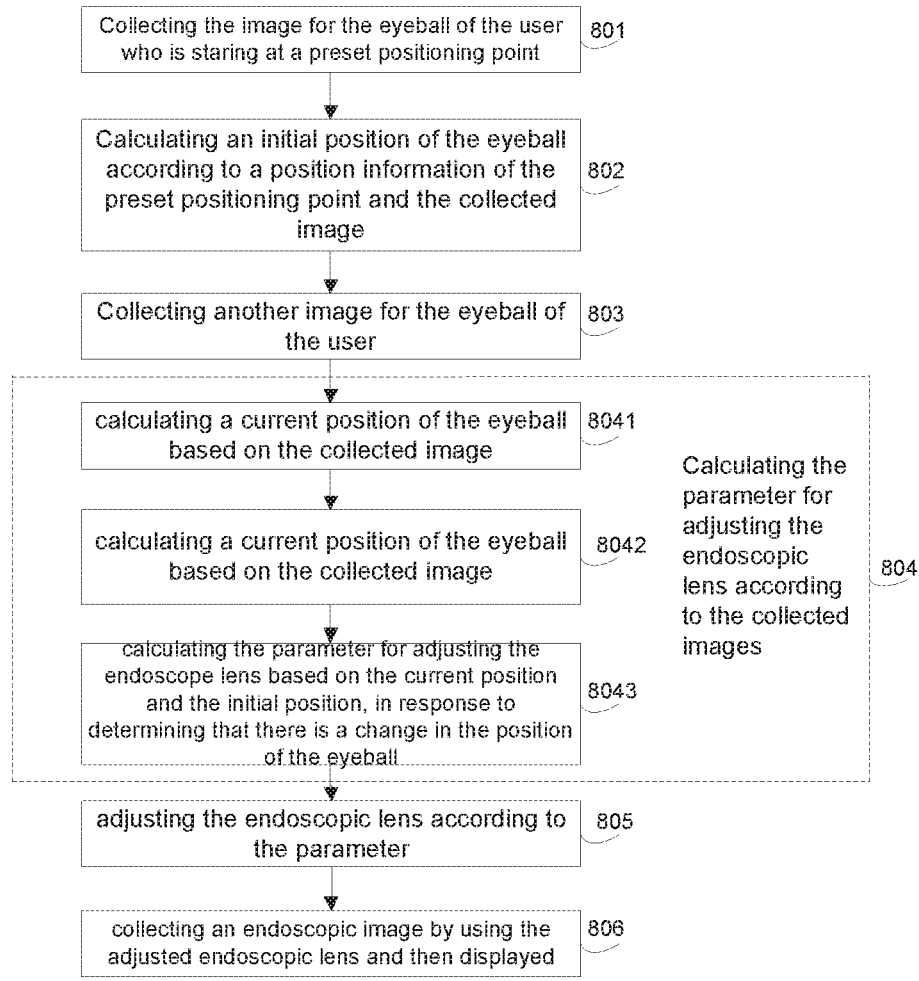
FIG. 8 shows a flowchart illustrating a method for controlling an endoscope according to another embodiment of the present disclosure.

There are provided another embodiment illustrating an method for controlling the endoscopic lens. As shown in FIG. 8, the method 80 for controlling the endoscopic lens according to the embodiment of the present disclosure may include the following steps.

In step 801, the image for the eyeball of the user who is staring at a preset positioning point is collected.

In step 802, an initial position of the eyeball is calculated according to a position information of the preset positioning point and the collected image.

In step 803, another image for the eyeball of the user is collect.

In step 804, the parameter for adjusting the endoscopic lens is calculated according to the collected images.

In step 805, the endoscopic lens is adjusted according to the parameter.

In step 806, an endoscopic image is collected by using the adjusted endoscopic lens and then displayed.

For an example, calculating a parameter for adjusting an endoscope lens of the endoscope based on the collected image comprises: calculating a current position of the eyeball based on the collected image; comparing the current position with an initial position of the eyeball, and determining whether there is a change in the position of the eyeball according to a comparison result; and calculating the parameter for adjusting the endoscope lens based on the current position and the initial position, in response to determining that there is a change in the position of the eyeball.

Those skilled in the art should understand that the foregoing descriptions are merely specific embodiments of the present disclosure and are not intended to limit the present disclosure. Any modifications, equivalent replacements, and improvements made within the spirit and principle of the present disclosure should all be comprised in the scope of the present disclosure.

What is claimed is:

1. An endoscope apparatus, comprising:
   an image collector, configured to collect an image for an eyeball of a user;
   a controller, configured to calculate a parameter for adjusting an endoscope lens of an endoscope based on the collected image;
   the endoscope, comprising the endoscope lens and configured to collect an endoscopic image by using the endoscope lens, and adjust a position and an orient the endoscope lens according to the parameter; and
   a display, coupled to the controller, and configured to display an initial image and the endoscopic image;
   wherein the image collector is further configured to collect an initial image of the eyeball of the user who is staring at a plurality of preset positioning points;
   wherein the controller is further configured to:
   calculate an initial position of the eyeball based on a relationship between position information of the plurality of preset positioning points and the initial image of the eyeball of the user;
   calculate a current position of the eyeball based on a current image of the eyeball of the user;
   compare the current position with the initial position of the eyeball, and determine whether there is a change in the position of the eyeball according to a comparison result; and
   calculate the parameter for adjusting the endoscope lens based on the current position and the initial position, in response to determining that there is a change in the position of the eyeball;

wherein the controller is further configured to determine an image of the eyeball of the user staring at the plurality of preset positioning points for a time greater than a first preset time, as the initial image of the eye ball, and determine an image of the eyeball of the user staring at an interested region in the endoscopic image for a time greater than a second preset period, as the current image for the eyeball.

2. The endoscope apparatus of claim 1, wherein the endoscope comprises:
   a rod for operating an endoscope lens, comprising a body, an adjustable sub-rod, a first motor and a second motor, wherein a first end of the adjustable sub-rod is fixed to the body rotatably and retractably, and the first motor is configured to drive the adjustable sub-rod to stretch or retract in an axial direction, and the second motor is configured to drive the adjustable sub-rod to rotate about the first end;
   the endoscope lens, disposed on the adjustable sub-rod and configured to collect an endoscopic image; and
   a controlling device, configured to control at least one of the first motor and the second motor according to the parameter for adjusting the endoscope lens.

3. The endoscope apparatus of claim 2, wherein the endoscope further comprises a pressure sensor and an alarm device;
   wherein the pressure sensor is disposed at a second end of the adjustable sub-rod and configured to detect an external pressure applied on the second end of the adjustable sub-rod and to convert the detected external pressure into an electrical signal;
   the controlling device is configured to calculate a pressure data according to the electrical signal, and to send an alarm prompting information to the alarm device in response to the pressure data exceeding a preset pressure threshold; and
   the alarm device is configured to send an alarm in response to receiving the alarm prompting information.

4. The endoscope apparatus of claim 2, wherein the controlling device is further configured to:
   receive the endoscopic image collected by the endoscopic lens; and
   send the endoscopic image to the controller.

* * * * *